(12) United States Patent
Smela

(10) Patent No.: US 6,360,615 B1
(45) Date of Patent: Mar. 26, 2002

(54) WEARABLE EFFECT-EMITTING STRAIN GAUGE DEVICE

(75) Inventor: Elisabeth Smela, Silver Spring, MD (US)

(73) Assignee: TechnoSkin, LLC, Silver Spring, MD (US)

( * ) Notice: Subject to any disclaimer, the term of this patent is extended or adjusted under 35 U.S.C. 154(b) by 0 days.

(21) Appl. No.: 09/588,014

(22) Filed: Jun. 6, 2000

(51) Int. Cl.⁷ ................................................ G01L 1/22
(52) U.S. Cl. ................................................ 73/862.474
(58) Field of Search ...................... 600/595; 73/379.01, 73/800, 862.474, 862.392; 446/397

(56) References Cited

U.S. PATENT DOCUMENTS

| | | | |
|---|---|---|---|
| 4,557,275 A | 12/1985 | Dempsey, Jr. | |
| 4,803,096 A | 2/1989 | Kuhn et al. | |
| 4,820,229 A | 4/1989 | Spraggins | |
| 4,904,222 A | 2/1990 | Gastgeb et al. | |
| 5,429,140 A | 7/1995 | Burdea et al. | |
| 5,436,444 A | 7/1995 | Rawson | |
| 5,455,749 A | 10/1995 | Ferber | |
| 5,505,093 A | 4/1996 | Giedd et al. | |
| 5,648,753 A | 7/1997 | Martin | |
| 5,662,123 A | * 9/1997 | Goldman | 600/595 |
| 5,768,223 A | 6/1998 | Li et al. | |
| 5,962,839 A | 10/1999 | Eskildsen | |
| 6,032,530 A | * 3/2000 | Hock | 73/379.01 |
| 6,033,370 A | 3/2000 | Reinbold et al. | |
| 6,119,516 A | * 9/2000 | Hoch | 73/379.01 |
| 6,165,143 A | * 12/2000 | van Lummel | 600/595 |

FOREIGN PATENT DOCUMENTS

| | | |
|---|---|---|
| CA | 2184957 | 3/1998 |
| IT | 1291473 | 1/1999 |
| WO | WO 9604053 | 2/1996 |

OTHER PUBLICATIONS

De Rossi et al. Wearable Piezo and Thermoresistive Fabrics for Ergonomics and Rehabilitation; Centro "E. Piaggo"; Faculty of Engineering—Univ. of Pisa; whole document.*

H. H. Kuhn, "Characterization and Application of Polypyrrole–Coated Textiles," in *Intrinsically Conducting Polymers. An Emerging Technology*, M. Aldissi (Ed.), 1993, p 25, Kluwer, Dordrecht.

D. De Rossi, A. Della Santa, A. Mazzoldi, "Dressware: Wearable Piezo–and Thermoresistive Fabrics for Ergonomics and Rehabilitation," XIX International Conference of IEEE & EMBS, Chicago, 30 Oct. –2 Nov. 1997.

D. De Rossi, A. Della Santa, A. Mazzoldi, "Dressware: Wearable Hardware," Mat. Sci. Eng. C, 7(1) p31–35 (1998).

S. Carlson, "Sensing Subtle Tsunamis," Sci. Amer p. 76–77, May 1998.

* cited by examiner

*Primary Examiner*—Benjamin R. Fuller
*Assistant Examiner*—Andre Allen
(74) *Attorney, Agent, or Firm*—Nixon & Vanderhye P.C.

(57) ABSTRACT

A position/movement sensitive effect-emitting strain gauge device includes a responsive portion, such as an electrically conductive fabric, that can be stretched or relaxed and that changes an electrical property, such as resistance, when stretched or relaxed. The changeable electrical property of the responsive portion is detected by a regulating circuit, which sends a signal that depends on the detected electrical property to an effect-emitting component. The effect may be sound or light emission or the like. The shape of the responsive portion can be such as to allow it to fit over a body part, e.g., a tube shape would allow it to fit over an elbow. When worn, the electrical property of the responsive portion, and therefore the emitted effect, depends on the user's positions/movements.

21 Claims, 9 Drawing Sheets

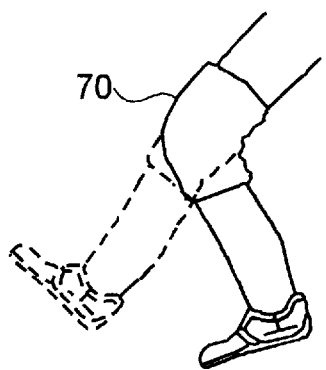 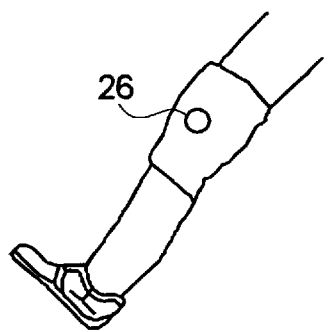
FIG. 4A          FIG. 4B
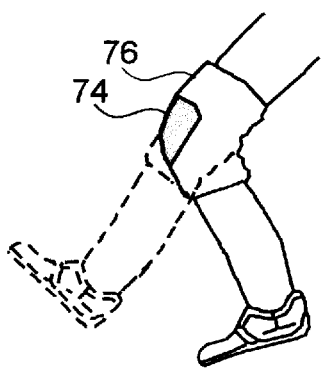
FIG. 5

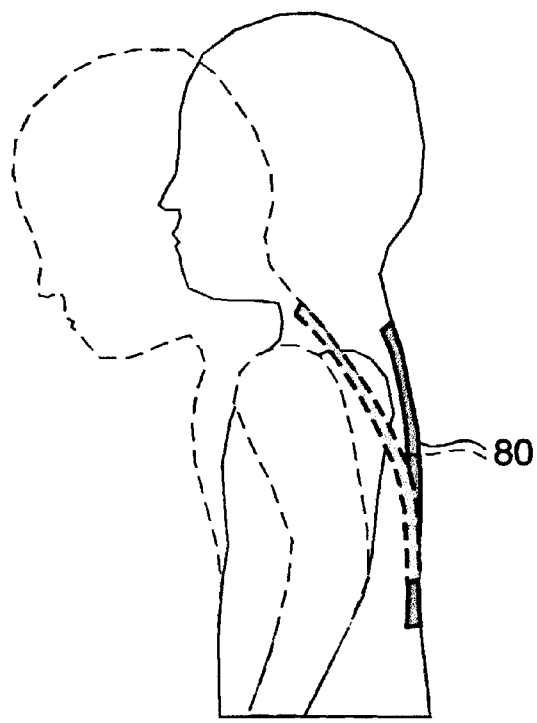 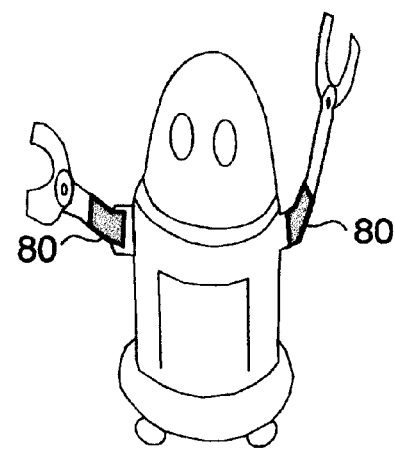
FIG. 6A FIG. 6B
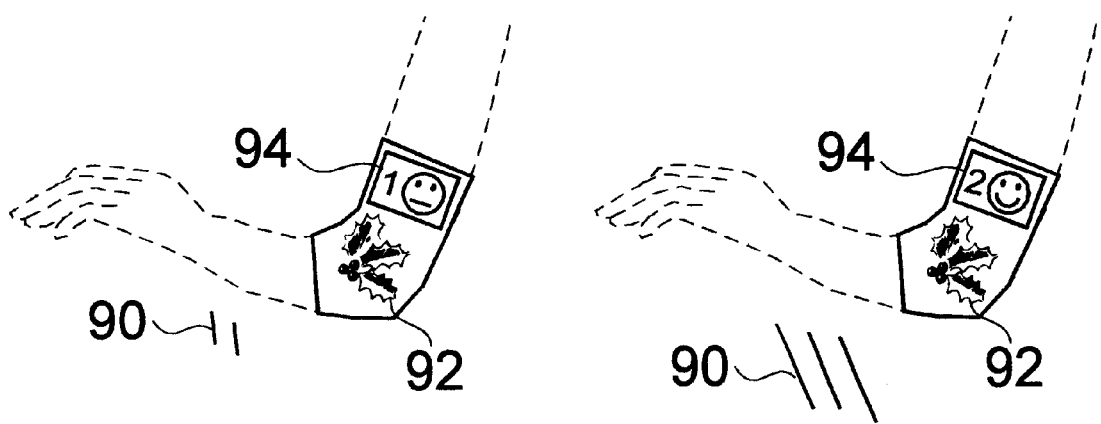
FIG. 7

WEARABLE EFFECT-EMITTING STRAIN GAUGE DEVICE

BACKGROUND

1. Field of the Invention

The invention relates to strain gauges, specifically to a device that generates effects, such as sounds or lights, in response to strain, such as caused by body position or movement.

2. Description of Prior Art

Toys

Toys with good play value allow variation and flexibility in play, as well as providing freedom for imagination and creativity. Interactivity, that is, the ability of a toy to respond to a user's action by emitting an effect, results in good play value. Sound effects have been used during play activity for many years, the sounds assisting the child to engage in imaginary activity or play. Children commonly act a role in the context of physical activity, and sound is ideally directly linked to this physical activity. Examples of toys with sound effects are crying dolls or pop guns. Lights have also been linked to play activity. Examples are light-sabers, glow-in-the-dark stars or necklaces, and hand held flashlights used to play light tag.

Wearable signal generating toys are especially advantageous and have been discovered to have particularly good play value. The benefits of wearability are that the toy interfaces well with the child's activity, that is, by adding to and enhancing the activity without any hindrance.

Signal generating wearable toys are known. One example with a sound effect device is described in Martin, U.S. Pat. No. 5,648,753 (1997). This patent is for a toy that can be worn on the arm. It has a transmitter that directs an infrared signal to a receiver that in turn plays a sound effect. In the embodiments described in the Martin patent, to play a sound effect the user must depress trigger switches. This has the disadvantage that it is disruptive for a child to manually push buttons on an object and play at the same time. Such prior art designs do not allow the user to control sound effects while playing with the toy in a more natural, realistic manner. Furthermore, the Martin device has the disadvantage that the sound effect is played to completion once the buttons are pushed, a disadvantage shared with most sound-making toys on the market. It is not possible to stop the sound once it starts, so the effect is not under the user's control.

Another such device is described in Spraggins, U.S. Pat. No. 4,820,229 (1989). Spraggins describes a wearable effect emitting gauntlet that can be worn on the arm. The effect consists of emitted lights and sounds to simulate lasers and phasors. This device is controlled by mechanical switches. The sounds are not linked to the child's natural movement during play, but must be activated by the hand not wearing the gauntlet. Furthermore, the sound loudness is not correlated with the degree of movement, nor can the light and sounds emitted reflect the speed of movement. Finally, a drawback of all switch-activated devices is that the area of the control switch is rather small. A distributed switch, i.e., one with a larger active area, would be more desirable.

Yanofsky, WO 9604053 (1996), describes a wearable toy glove that produces sounds stored in memory, with different sounds generated by different switches, pressure contact, or electrical contact. The tone generator includes a CPU which converts values stored in memory into an analog wave-form sent to a speaker to produce the recorded sound. The Yanofsky toy can be worn only on the hands. The glove may be cumbersome to wear, especially for small children. Furthermore, the device is not sensitive to very small movements.

Ferber, U.S. Pat. No. 5,455,749 (1995) describes a wearable article, such as a shirt, onto which current carrying materials have been printed. A battery, a current-operated sound and/or light emitting module, and a control means for controlling the operation of the current operated module can be mounted on the shirt. The emissions are unrelated to body position.

Rawson, U.S. Pat. No. 5,436,444 (1995) describes a sound-generating wearable motion monitor with possible toy applications. The Rawson device is based on a laser, optical fiber, and photo-receiver. The physical movement of this optical fiber generates a signal that is output to an amplifier. This technology is expensive and unlikely to withstand use by children. Furthermore, the device only emits a noise-like signal whose amplitude and average frequency mimic the motion, not noises that would delight children. Finally, the device is difficult to miniaturize so that it can be, for example, worn on a finger.

Reinbold et al., U.S. Pat. No. 6,033,370 (2000) describe an interactive force feedback device with toy applications. The device is a capacitive force sensor comprising a plurality of layers forming a force sensing detector whose output signal responds to pressure. The device is incorporated into objects such as squeeze balls or shoes for sensing applied force. This device is not wearable, nor is it sensitive to delicate movements: it is designed to measure significant forces.

Gastgeb et al., U.S. Pat. No. 4,904,222 (1990) describe toy swords and drumsticks that emit sounds and lights when they are repeatedly waved. The effects are produced by a piezoelectric element incorporated in the body of the toy that gives a transient voltage when flexed/bent. The toy is connected by a cable to the effect emitters, which generate one sound that varies in loudness proportionally with the oscillation of the sword or drumstick and another tone that varies when the frequency of the electrical signal exceeds 300 hertz. The toy is not wearable, but hand-held. It has the disadvantage that piezoelectrics cannot generate a d.c. response, so the signal must be oscillatory. Thus, static positions cannot generate sounds. Furthermore, the effects are produced only by flexing a stiff member, which is disadvantageous for many applications.

It would be further desirable that the effect emitting device could be incorporated into a variety of existing devices to make them more interactive. The effect emitting device thus incorporated should be inexpensive.

Rehabilitation

After an injury, a person may require rehabilitation to help regain the use of a limb. Rehabilitation and training are facilitated by feedback, which may be in the form of sound or light signals, small electric shocks, a temperature change, or touch by an actuator. Feedback is particularly useful if the intensity of the feedback signal is correlated with the magnitude (or other characteristics) of the motion. Such interactive devices allow a person to monitor his or her progress.

Devices that attach to the limb and provide audio feedback are known. A considerable number of biofeedback devices related to rehabilitation have been patented, and often these make use of sounds to provide feedback. However, such biofeedback systems are often immobile and complicated, or they are controlled by computer. Furthermore, many rehabilitation devices deliver a fixed feedback signal when a threshold is exceeded. For these devices, the intensity of the signal does not depend on the characteristics of the motion. Burdea et al., in U.S. Pat. No. 5,429,140 (1995), describe a rehabilitation system that employs a force feedback system, such as a force feedback glove, to simulate virtual deformable objects. This system is complex and comprises numerous components. Furthermore, this system is costly. Finally, this system is not readily wearable or portable.

Dempsey, U.S. Pat. No. 4,557,275 (1985) teaches a biofeedback system for rehabilitation therapy. The system includes a plurality of mercury switches arranged to respond to change in position of a body member. Circuitry responds to the closing of the switches to give distinct signals. The signal processing circuitry is housed within a console. Audible signals are delivered by headphones, and visible signals are provided by colored lamps. The Dempsey switches are complex and bulky, and the mercury poses a potential health hazard. The system does not provide feedback based on the extent of movement, but rather whether the movement has crossed some threshold that causes a switch to close.

Stasiuk, CA 2184957 (laid open 1998) describes a rehabilitation device that generates audio feedback indicative of a load applied by a limb (not the position or movement of a limb). A load sensor is attached to the limb, and the load signal is compared to a threshold signal. The feedback signal depends on the difference between the load and threshold signals. The load sensor comprises plates separated by insulators, forming a capacitor. Loading the sensor changes the plate spacing and thus the capacitance. A control unit is worn on a belt, and headphones provide the audio feedback. This is a portable, wearable system. However, it is based on compression rather than stretching, and thus is not adaptable to being worn on body joints, such as finger joints or knees. The control unit is large, approximately 150 mm×75 mm×50 mm, and hence cannot be worn on small limbs such as fingers.

Strain Gauges

Strain gauges, i.e., devices that measure change in length, are known and are commercially available. Strain gauges may utilize a change in an electrical property of a material, such as resistance or capacitance, to measure strain Examples of strain gauges based on films of the conjugated polymer polyaniline and on ion-implanted polymers are given in Giedd et al., U.S. Pat. No. 5,505,093 (1996). Strain gauges based on conjugated polymer coated textiles are described below.

Textiles That Sense Stretching

Electrically conductive textiles that change resistance upon stretching (i.e., under strain) and/or exposure to heat are known. De Rossi et al. have shown that polypyrrole coated LYCRA shows a piezoresistive effect (see De Rossi et al., *Mater. Sci. Eng.* C, 7(1), 31–35 (1998); De Rossi et al., "Dressware: Wearable piezo- and thermoresistive fabrics for ergonomics and rehabilitation," presented at the XIX Ann. Intl. Conf. IEEE and EMBS, Chicago, Oct. 30–Nov. 2, 1997; and De Rossi et al. patent IT 1291473 (1997)). De Rossi et al. believe that this piezoresistive effect is due to an increase in the number of contacts between the fibers woven into the fabric when the fabric is stretched. A decrease in resistance of 20% was reported for an increase in length of 1% obtained by stretching. These materials are therefore sensitive strain gauges. Metal coated fabrics were expected by De Rossi et al. to show the same piezoresistive effect. The deposition of metallic films using vacuum deposition was counted among the usable techniques for producing piezoresistive fabrics in the invention by De Rossi et al., patent IT 1291473 (1997). Other methods mentioned for depositing conducting layers on various materials included writing a pattern by ink-jet printing.

De Rossi in his patent IT 1291473 teaches a method and an apparatus for measuring the movement of body segments. The apparatus is a glove comprising sensing areas made of conjugated polymer coated textiles, wiring segments that transfer the signal to a signal processing unit, a personal computer, and software for interpreting the signal.

The De Rossi system is wearable, but not portable. In addition to sensing regions, it comprises textile zones of high conductivity for transferring the sensed signal to a device for signal processing. It is also complex, requiring a computer and software for calibration and interpretation of the signals. Importantly, it does not emit any effects, but instead displays processed results on a computer screen.

BRIEF SUMMARY OF THE INVENTION

A wearable, wireless (no communication with computer necessary) device, consisting of a stretchable responsive material with electrical properties that change upon stretching, a power source, a regulating electrical circuit that generates a signal in response to stretching or relaxing the stretchable material of the device, and an electrically controlled effect emitter that produces an effect, such as a sound, light, or infrared light, in response to the signal from the regulating circuit. The magnitude of the emitted effect can be directly modulated by the degree of bending of a wearer's body joint (elbow, knee, finger, shoulder, back, etc.) or by extension of a body part (arm, leg, neck, etc.) or by the speed or number of a wearer's movements. The device can also be incorporated into other objects, such as stuffed toys. The device can be used for a wide variety of purposes, including as a toy, for biofeedback purposes, and as a remote control device.

Objects and Advantages

Accordingly, one object of the present invention is a wearable effect-emitting device. This has the advantage of allowing effects to be produced portably and without hindrance.

Another object is an effect-emitting device that produces effects correlated with body positions or movements. This provides the advantage that the effects are due to the body positions or movements and that no extra motions, such as pushing buttons or switches, are necessary.

Another object is to provide an effect-emitting device for which the magnitude or type of effect depends on the magnitude, speed, or other characteristics (static or dynamic) of the user's movements. Linking the effect to the activities of the user, rather than a predetermined program, makes the device more interesting and fun. This has the advantage of providing feedback and good play value, as well as making it possible for those with limited motion to use the device.

Another object is to provide an effect-emitting device that can be worn on any bendable or stretchable body segment. This provides the advantage that different effect emitters can be worn on different parts of the body, or the same effect emitter can be placed on different parts of the body. This allows a number of different effects to be produced by the wearer, the sequence of which is controlled by the wearer.

Another object is to provide an effect-emitting device controlled by the deformation of a potentially large area instead of a small switch. This allows additional design options as well as increased ease of use and/or enjoyment of the articles.

Another object of the present invention is to provide an effect-emitting device that can be incorporated or designed into other articles such as toys and the like. This allows increased enjoyment of existing articles.

Another object of the present invention is to provide an inexpensive effect-emitting device. This has the advantage of making the device affordable in a variety of price-sensitive markets.

Another object of the present invention is to provide an effect-emitting device that does not rely on a computer. This has the advantage of portability and low cost, and well as freeing the user from a tangle of wires.

Another object of the invention is a robust effect-emitting device. This has the advantage of allowing the device to stand up to rough use, such as by playing children.

Another object of the invention is an effect-emitting device that is sensitive to small movements. This allows the amplification of small differences in position or speed, which is especially useful for rehabilitation or training. It also has the advantage of making use of naturally small movements, such as ear wiggling, to produce effects.

Another object of the invention is to provide an effect-emitting device whose effects can cause delight. This has the advantage of good play value. For rehabilitation or training, it has the advantage of making the use of the device more pleasant.

Another object of the invention is to provide an effect-emitting device that can be miniaturized. This has the advantage of making the devices inexpensive, light-weight, and more wearable on small body parts.

DESCRIPTION OF THE DRAWINGS

FIG. 4A shows the stretchable responsive component being worn on a knee as a cuff.

FIG. 4B shows an effect emitter on the knee cuff and signal emission upon flexing of the knee.

FIG. 5 shows a knee cuff with a stretchable component only over a knee cap.

FIG. 6A shows the wearable effect emitting device in the form of a strip worn on the back.

FIG. 6B shows the inventive device in the form of strips being worn on a robot's arms.

FIG. 7 shows the inventive device decorated with a seasonal decoration; the effect emitter is a display whose output depends on the wearer's speed of movement.

List of Reference Numerals

| | |
|---|---|
| 20 | responsive stretchable component |
| 22 | regulating circuit |
| 24 | power supply(ies) for circuit and effect emitter |
| 26 | effect emitter |
| 30 | fastening strap means of attaching the inventive device to a body |
| 32 | hook-and-loop fastening mechanism |
| 34 | connector between regulating circuit 22 and one side of responsive component 20 |
| 36 | connector between regulating circuit 22 and another side of responsive component 20 |
| 40 | polypyrrole treated knitted polyester fabric whose resistance changes upon stretching |
| 40A | one side of the stretchable responsive component |
| 40B | another side of the stretchable responsive component |
| 42 | battery |
| 44 | first diode |
| 46 | second diode |
| 48 | variable resistor (potentiometer) |
| 48A | a terminal of potentiometer 48 |
| 48B | another terminal of potentiometer 48 |
| 48C | the variable terminal of potentiometer 48 |
| 50 | battery |
| 52 | op amp |
| 54 | resistor |
| 56 | buzzer |
| 58 | resistor |
| 70 | stretchable responsive component in the shape of a cuff |
| 74 | stretchable responsive component in the shape of a patch |
| 76 | conventional fabric component in the shape of a cuff |
| 80 | inventive wearable effect emitting device(s) |
| 90 | lines indicating speed of movement |
| 92 | decoration |
| 94 | display |
| 100 | socket into which various effect emitters, such as 101–106, can be placed |
| 101 | sound emitting effect emitter |
| 102 | electric shock emitting effect emitter |
| 103 | temperature changing effect emitter (heater or cooler) |
| 104 | light emitting effect emitter |
| 105 | infra-red or radio wave (invisible electromagnetic radiation) emitting effect emitter |
| 106 | movement-causing effect emitter (actuator) |
| 110 | hoop member of toy |
| 112 | central portion of toy |
| 114 | means of attaching central portion to hoop |
| 120 | trampoline |
| 121 | frame of trampoline |
| 122 | central portion of trampoline that is jumped upon |
| 124 | means of attaching central portion to frame of trampoline |
| 126 | loudspeaker |
| 128 | power cord |
| 129 | hook |
| 140 | stretchable dielectric |
| 142 | interdigitated implanted electrodes |

DETAILED DESCRIPTION OF THE INVENTION

Figure 1:
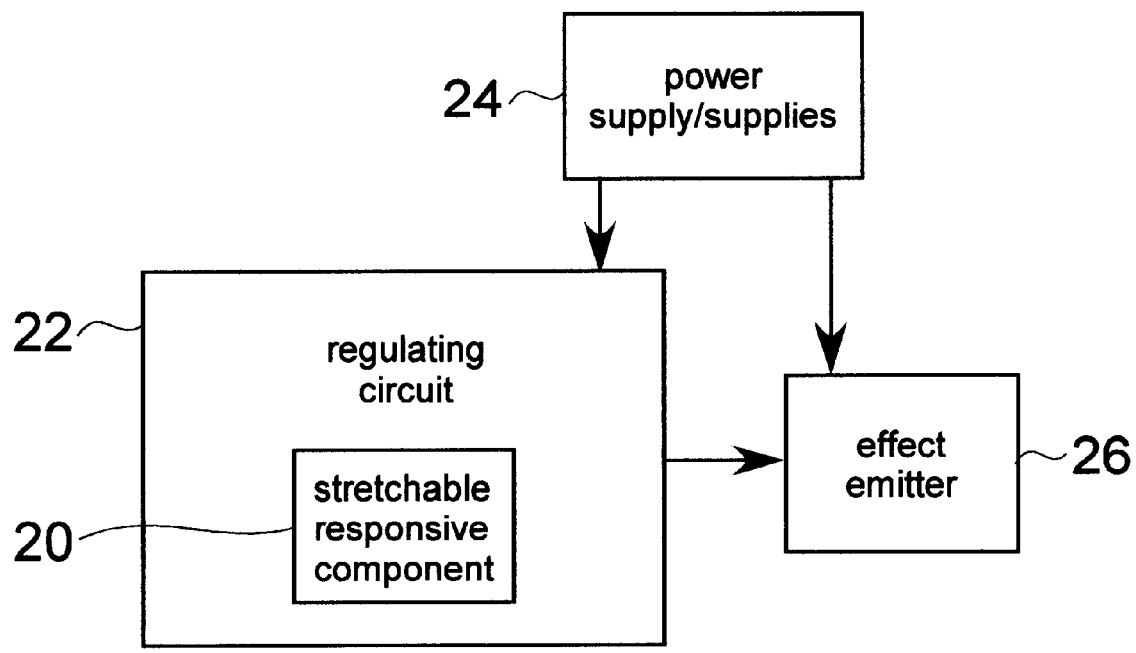
FIG. 1 shows a schematic diagram of the inventive wearable effect emitting device.

Physical Description (FIG. 1 and FIG. 2)

The wearable effect emitting device converts static positions or dynamic movements, especially body positions and movements, into effects, such as sound or light emission.

FIG. 1 shows a schematic representation of the major components of the wearable effect emitting device. A stretchable (extensible) responsive component 20, whose electrical properties change with stretching (strain), is part of a regulating circuit 22. (The responsive component 20 can be thought of as a variable impedance, one element in the circuit 22 whose output depends on the impedance.) The circuit 22 is powered by one or more power supplies 24. The circuit 22 outputs a signal to an effect emitter 26. The effect emitter 26 is also powered by one or more of the power supplies 24.

In its simplest configuration, the means for converting motion into a signal comprises a conducting polymer coated fabric that changes its resistance when stretched, a circuit that detects and amplifies this resistance change, a battery, and noise or light makers. Other configurations are discussed below.

Figure 2A:
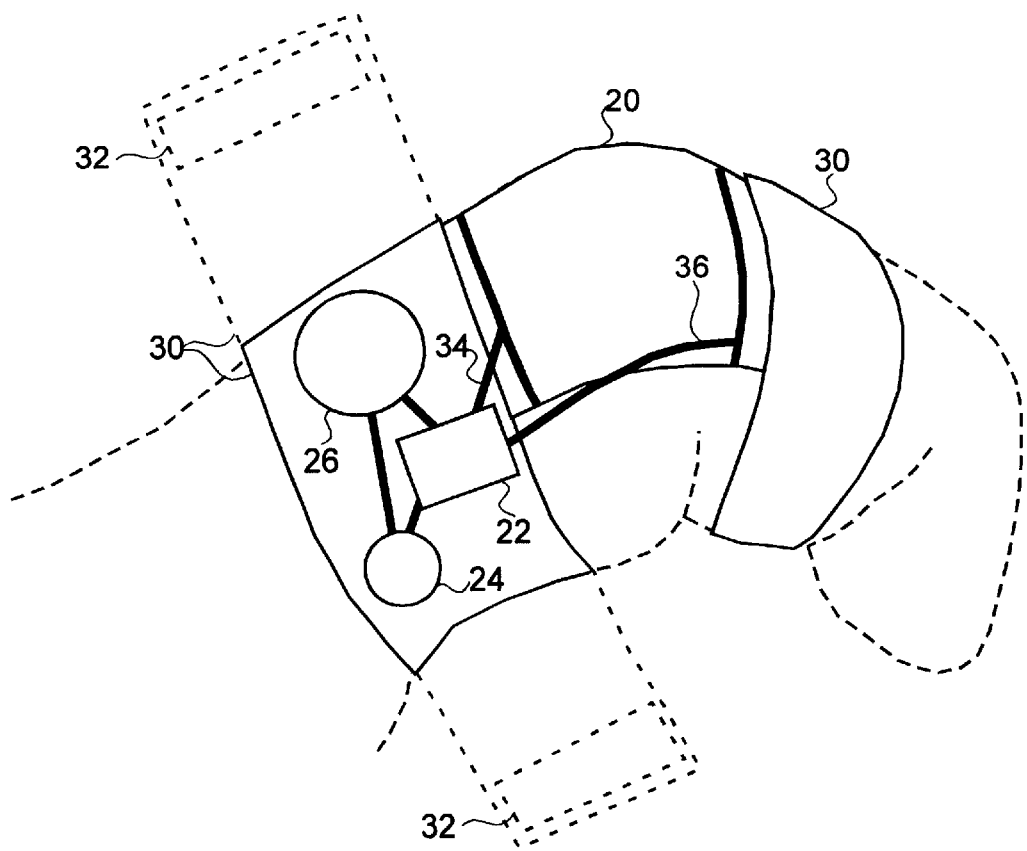
FIG. 2A shows an example of the effect emitting device worn on a finger.

FIG. 2A shows a wearable effect-emitting device being worn on a finger. (This figure is for illustrative purposes only and should not be construed as limiting the possible configurations or connections.) In this example, the device is attached to the finger by means of fastening straps 30 that use a hook-and-loop mechanism 32 (such as VELCRO) for closing. These straps allow the device to be adjusted for an individual finger. The power supply 24 is connected to the regulating circuit 22 and the effect emitter 26. The circuit 22 is connected to the effect emitter 26. The responsive component 20 is connected on both sides into circuit 22 by connecting means 34 and 36. This allows the circuit 22 to detect the electrical properties of responsive component 20. Connecting means 34 and 36 could be made of flexible conductive insulated wire to allow movement as the user flexes his/her finger.

Below is a general discussion of the various device components that may be used in the effect-emitting strain gauge device. This discussion is for illustrative purposes only and should not be construed as limiting the invention.

Stretchable Responsive Components

Electrically conductive, conjugated polymer fibers and fabrics are known. Typical conjugated polymers are polypyrrole and polyaniline. Polypyrrole coated fabrics can be produced as follows. A porous substrate, such as cloth, can be dipped into an oxidant/dopant solution, dried, and then treated with pyrrole to produce an electrically conductive polypyrrole deposit in the interstices of the substrate. (See, e.g., Kuhn et al., U.S. Pat. No. 4,803,096 (1989); Kuhn, "Characterization and application of polypyrrole-coated textiles," *Intrinsically Conducting Polymers-An Emerging Technology*, Kluwer, Dordrecht, p. 25, 1993; and De Rossi et al., "Dressware: wearable hardware," *Mat. Sci. Eng.* C 7(1):31–35 (1998).) Polyaniline can be deposited on substrates in a similar way.

Electrically conductive textiles have been used for a variety of purposes. Several examples will demonstrate this. Conducting polymer coated materials are useful when corrosion or lack of adhesion prevents the use of metal-coated fabrics. Milliken's polypyrrole-coated fabrics (trade name CONTEX) show dissipation of static electricity for applications in conveyer belts, upholstery fabrics, carpets, and the like. For low frequency EMI shielding applications, coated fabrics with a surface resistance below 1 ohm/square can be produced. The military has made use of polypyrrole and polyaniline-coated fabrics to create radar-absorbing materials for use in camouflage netting applications.

Particularly useful as piezoelectric materials are polypyrrole/LYCRA, polypyrrole/nylon, or polypyrrole/polyester because of their elasticity, ideal conformation to the human body, and high piezoresistive coefficients. A major supplier of these electrically conducting, conjugated polymer coated fabrics is the Milliken Research Corp., Spartenburg, S.C. (USA). Such material may be prepared according to Kuhn et al., U.S. Pat. No. 4,803,096, assigned to Milliken.

Films of conjugated polymers or ion-implanted polymers, as described by Giedd et al. U.S. Pat. No. 5,505,093 (1996), may also be used.

Swift Textile Metalizing LLC, Bloomfield, CT, provides electrically conductive, flexible metal-coated fabrics including wovens, nonwovens, and knits, filaments, and yarns.

Signal-Emitting Components

Sound effect emitters that can be used in toys, greeting cards, and the like are known and are commercially available. Sound emitters were employed in the patents described above (Prior Art). Electromagnetic energy emitters, including emitters of light, infra-red light, and radio frequency, are known and are commercially available, and include light emitting diodes, lasers, incandescent bulbs, and liquid crystal displays. These and other components are well known and are commercially available. Some examples are given below.

Sound emitters are well established technology. Miniaturized sound emitters have been used in toys and greeting cards for many years.

Light emitters are also well established. Small lights and displays are ubiquitous in electronic equipment.

Infrared emitters are found in most remote-control devices. Temperature controllers are found in miniature form as Peltier effect devices that can both cool and heat.

Electric shocks can be delivered by a simple power supply. Actuators that can be miniaturized and electrically activated include motors, piezoelectrics, electrostatic mechanisms, and microelectromechanical systems.

Power Supplies

Power supplies are well known and commercially available. The power supply can be any of a number commonly used to power devices, including batteries, solar cells, wind-up spring mechanisms, wall current (alternating current 60 Hz, 110 V or 50 Hz, 220 V), and self-winding watch flywheel mechanisms. Batteries are preferred.

Regulating Electrical Circuits

Regulating/sensing circuits may be quite simple, and, in general outline, are previously known. An example of a sensing circuit containing a resistance sensor and zero-adjust can be found in Carlson, Scientific American, May 1998, pp 76–77. Examples of effect-regulating circuits can be found in Martin U.S. Pat. No. 5,648,753 (1997), Spraggins U.S. Pat. No. 4,820,229 (1989), and Reinbold et al. U.S. Pat. No. 6,033,370 (2000). Design of appropriate circuits is well known to those skilled in electrical engineering arts.

Operation of the Invention (FIG. 1 and FIG. 2)

The circuit 22 outputs a signal to the effect emitter 26 that depends on the electrical properties of the stretchable responsive component 20, the rate of change of the electrical properties of the stretchable component 20, the number of times the electrical properties of the stretchable component 20 have changed, or on other static or dynamic electrical properties of responsive component 20.

In one configuration, the stretchable responsive component 20 is worn over a body joint (or a plurality of body joints) and is stretched when this joint is bent, as shown in FIG. 2A. Alternatively, the stretchable responsive component 20 can be worn in such a manner that it is stretched by extending a body part (e.g. pushing out the belly). The stretchable responsive component is a part of the electrical circuit, so the resulting value (or change in value, or rate of change in value) of the electrical property causes a change in the signal applied to the effect emitting component. The emitted effect is often in the form of sound or light. In other configurations, the emitted effect is something other than conventional sound or light, such as radio frequency electromagnetic radiation, infrared light, ultrasound, an electric shock, a movement, or a change in temperature.

In FIG. 2A, when the responsive component 20 is stretched by bending the finger, its electrical property change is detected by regulating circuit 22, and a signal is sent to effect emitter 26. The magnitude of the signal is proportional to the degree of finger bending. When the finger is straightened, effect emission ceases immediately.

Figure 2B:
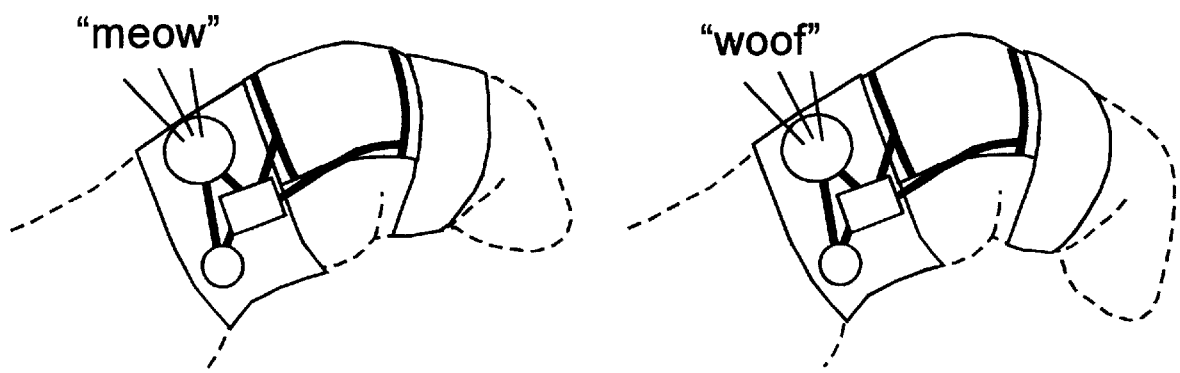
FIG. 2B shows an example of the emitted effect depending on the degree of bending of a finger.

In FIG. 2B, the type of signal that is emitted, rather than its magnitude, depends on the degree of bending of the finger. For a little bending, one effect is emitted, and for more bending a different effect is emitted. The number of effects can vary depending on how many effects the maker intends to provide to the user, or, for a programmable effect emitter, how many effects the user provides.

Other objects and features of the wearable effect emitting strain gauge device will become apparent from the following examples considered in conjunction with the accompanying drawings. It is to be understood that the drawings and descriptions are designed solely for the purposes of illustration and not as a definition of the limits of the invention, for which reference should be made to the claims. It should be further understood that the drawings are not necessarily drawn to scale and that, unless otherwise indicated, they are merely intended to conceptually illustrate the structures and procedures described herein.

EXAMPLE 1

Figure 3:
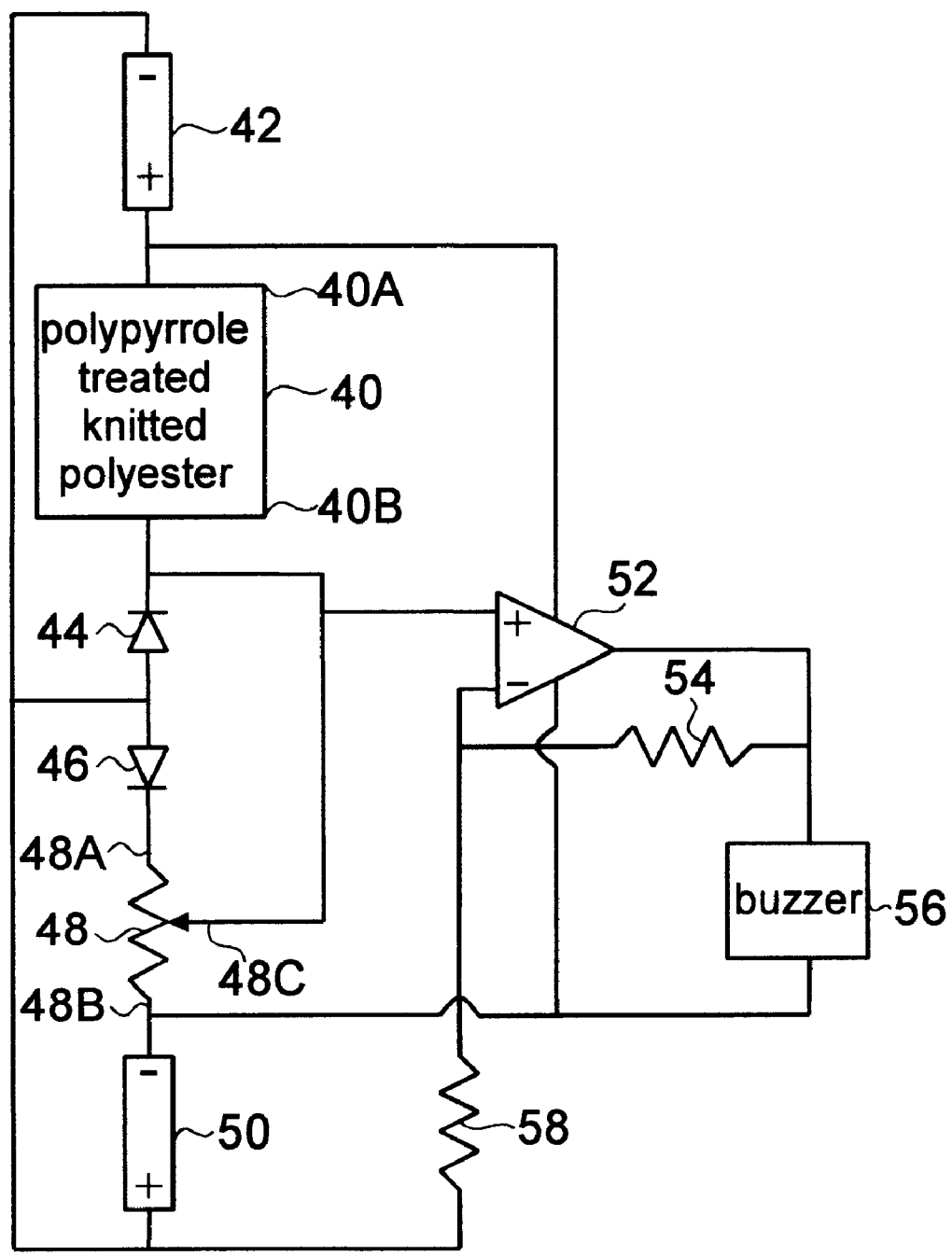
FIG. 3 shows a circuit diagram of one embodiment of the wearable effect emitting device.

Basic Circuit (FIG. 3)

FIG. 3 shows a circuit diagram of an embodiment of the wearable effect emitting strain gauge device. The stretchable component 40 is a piece of polypyrrole-treated knitted polyester. The polyester fabric, sold under the trade name CONTEX®, was obtained from Milliken Research Corporation, Spartanburg SC. One side of the stretchable component 40 is connected to the positive terminal of a first 1.5 V AA battery 42. A second side of the stretchable component 40 is connected to the cathode terminal of a first diode 44. Electrical connection to stretchable component 40 is made with alligator clips or by weaving an unshielded wire through the fabric. (Other connecting means that may be used include metal-particle containing pastes and glues, compositions as described in Ferber, U.S. Pat. No. 5,455,749 (1995), low-temperature solder, and other means known to those in the art.) The coated polyester fabric is fastened to a finger as shown in FIG. 2 by straps sewn onto it with attached hook-and-loop fasteners. The diode 44 can be purchased from Radio Shack, and is a Si diode model IN4001 rated for 50 V, 1A. The second side of the fabric 40 is further connected to the positive input of an op amp 52. The op amp 52, model ICL 7611, is available from Maxim Integrated Products, Sunnyvale Calif. The negative terminal of battery 42 is connected to the anode terminal of diode 44. The positive terminal of the battery 42 is further connected to the positive power input of op amp 52. The anode terminal of first diode 44 is further connected to the anode terminal of a second diode 46. The diode 46 is identical to the diode 44. The anode terminals of diodes 44 and 46 are further connected to the positive terminal of a second 1.5 V AA battery 50. The negative terminal of the battery 50 is connected to a terminal 48B of a potentiometer 48. Another terminal 48A of potentiometer 48 is connected to the cathode terminal of diode 46. The variable third terminal 48C of potentiometer 48 is connected to the positive input of op amp 52. The potentiometer is a model 503M 8805 available in the potentiometer and trimmer assortment 271–1605 from Radio Shack. The negative input of op amp 52 is connected to a terminal of a 100 kΩ resistor 58 and to a terminal of a 1 MΩ resistor 54. The resistors 54 and 58 are available from Radio Shack in the metal-film resistor assortment 271–309A and are rated at ¼ watt, 1% tolerance. The other terminal of resistor 58 is connected to the positive terminal of battery 50. The negative power supply of op amp 52 is connected to the negative terminal of battery 50. The output of op amp 52 is connected to the other terminal of resistor 54, and the output of op amp 52 is also connected to a terminal of a buzzer 56. The buzzer is a model 273–053A 3 V DC Mini Buzzer rated at 1.5 to 3 V d.c., 15 mA available from Radio Shack. The other terminal of buzzer 56 is connected to the negative terminal of battery 30.

The op amp 52 is connected to resistors 54 and 58 in a manner well known to those in the art to result in amplification at the output of op amp 52 of the voltage at the positive input of op amp 52. The parts of the circuit 40, 42, and 44 are mirrored by the parts 48, 50, and 46, respectively. When the resistance between terminals 48B and 48C of potentiometer 48 is equal to or greater than the resistance of the stretchable component 40, the positive input of op amp 52 is zero volts, and no signal is output. The user can adjust the potentiostat 48 so that the resistance between terminals 48B and 48C is equal to the resistance of the stretchable component 40 in its relaxed, unstretched state. When, due to stretching by bending the finger, the resistance of stretchable component 40 decreases below the threshold resistance between terminals 48B and 48C of potentiometer 48, a small positive voltage is experienced by the positive input of op amp 52, causing the op amp to amplify the non-zero voltage signal. The amplified voltage causes the buzzer 56 to buzz. When the fabric is relaxed so that it returns to its original length, the positive input of op amp 52 returns to zero volts, and the buzzer stops buzzing.

Conjugated polymer coated fabrics have a number of advantages. They are comfortable to wear, easy to sew together to form various garments or parts of other cloth objects, and the sewing results in the formation of electrical contact between various conducting fabric pieces so that no additional electrical connections are necessary. Furthermore, the ΔR/R is large and almost linearly proportional to ΔL/L up to 1% (see De Rossi et al., *Mater. Sci. Eng. C*, 7(1), 31–35 (1998)), allowing small stretches to be easily detected and the emitted effects to be made proportional to the degree of stretching.

EXAMPLE 2

Light Emitting Diode

In another embodiment of the wearable effect emitting device, the buzzer 56 in FIG. 3 is replaced by a light emitting diode. The light emitting diode is part of a light emitting diode assortment, number 276–1622, purchased from Radio Shack.

When the polypyrrole-treated knitted polyester stretchable component 40 is stretched, the diode lights up. When the fabric is not stretched, the diode is off.

EXAMPLE 3

Miniaturization

In a preferred embodiment of the invention, the regulatory circuit, effect emitting components, and power supply(ies) are miniaturized because light weight and compactness are desirable. The circuitry, for example, can be produced on a printed circuit board. This procedure is known to those skilled in the art, and one can arrange to have custom printed circuit boards manufactured in the commercial marketplace. Alternatively, part of the circuit can be miniaturized on an integrated circuit (IC) chip. Chip foundries exist that can perform this task. The speaker of a sound emitter may also be miniaturized. Such speakers are available commercially. The batteries may be watch batteries or other small lithium batteries.

EXAMPLE 4

Stretchable Resistance-Changing Materials

In another embodiment, the responsive component is a metal-coated fabric. In still other embodiments, the responsive component is made a) entirely of a conducting polymer, e.g., polypyrrole or polyaniline, b) an ion implanted polymer, c) a blend of another material with a conjugated polymer, d) a metal particle or carbon filled polymer, or e) a different material sensitive to strain. The possibility of using a film of conducting polymer or an ion implanted polymer as a stain gauge was taught by Giedd et al. in U.S. Pat. No. 5,505,093 (1996). It is well established in the literature that blending conjugated polymers, metal particles, carbon, or other conductors with conventional insulating polymers results in a conducting blend if the fraction of the conducting component exceeds a percolation threshold. Thus, woven articles of these blends or materials coated with these blends are expected to show the same piezoresistive effect. It is also well established that near the percolation threshold, stretching the blend may increase the distance between conducting regions such that the conductivity of the blended article drops. This is a different mechanism whereby the resistance of a stretchable component, such as a rubber, may be changed by stretching and is included among the usable materials of this invention.

As pointed out in De Rossi et al. IT 1291473 (1997), individual threads can be covered with conjugated polymers or metals and then woven into fabrics. If other, conventional fibers are used in the weaving, then the sensing element can be patterned. This may be done for aesthetic reasons or to control the location of the sensing zones.

EXAMPLE 5

Cuff Shape (FIG. 4)

In a preferred embodiment of the invention, the stretchable component is in the form of a cuff, band, or tube. The cuff is worn on a bendable portion of the body, such as a finger, wrist, elbow, neck, knee, ankle, or on an expandable part of the body, such as the waist, or on the head over the ears. FIGS. 4A and 4B show a cuff-shaped stretchable component 70 being worn on a knee. Bending the knee causes the stretchable responsive component to stretch over the knee-cap and the effect emitter 26 to activate. The stretchable cuff 70 can be worn either over or under clothing. The cuff may be used as a feedback device for medical purposes. For example, if a joint is to be held immobile, the cuff will give an alarm when the joint is moved; as an example, such a cuff may be worn on the neck.

Additional components may be used to enable the responsive component to be shaped into a cuff. These components allow the ends of a strip of the responsive component to be fastened together. Fastener components may be hook-and-loop fasteners, snaps, zippers, buttons, etc. Alternatively, the ends of a strip of the responsive component may be sewn together, and the cuff slid onto the body part.

EXAMPLE 6

Additional Components (FIG. 5)

In another embodiment, pieces of conventional fabric or other materials are sewn or otherwise attached to the stretchable responsive component. These provide non-stretching regions for improved structural or mechanical properties or provide regions of the wearable device that do not generate a signal. FIG. 5 shows a knee cuff with the stretchable component 74 only over the front of the knee. The remainder of the knee cuff 76 is made of a conventional pliable fabric or plastic using conventional sewing, gluing, or molding techniques. Additional structural components may also include plastic housings to protect the circuitry and/or effect emitting components or to house batteries. The effect emitter, circuitry, and power supply may be mounted on these additional components.

EXAMPLE 7

Strip Shape (FIG. 6)

In another embodiment, the device is worn in the shape of a strip. The strip is attached to clothing using e.g. pins or Velcro, or is attached to the body using tape or adhesive.

FIG. 6A shows the wearable effect emitting device 80 in the form of a strip worn on the back. This feedback device may be used to improve posture.

In this embodiment and the cuff embodiment, the wearer can be a living human or an animal, a plant, a robot or robotic toy, a piece of machinery, a vehicle, or other thing capable of movement, either autonomously or with the aid of gravity, wind, etc. FIG. 6B shows the inventive device 80 in the form of strips being worn on a robot's arms.

EXAMPLE 8

Decorations (FIG. 7)

The device is decorated in various ways to improve its appearance and identify its behavior. FIG. 7 shows the inventive device worn as a cuff decorated with a seasonal decoration 92. The decoration 92 may be an integral part of the stretchable component, for example the pattern may be woven using a combination of conjugated polymer coated thread and conventional thread. The decoration 92 may alternatively be an article that is attached by, for example, sewing. Patterns may be printed, screened, or painted over the stretchable resistance-changing component or over additional components as described above. Other materials may be attached to the device, such as sequins. The decorations may correspond to the effects emitted. For example, a dog's face may be represented on the wearable effect emitting device for a sound emitter that produces barking noises. The decorations may be used to give a nice appearance to the housing for batteries or circuitry or other components of the device.

EXAMPLE 9

Sound Generators

In another embodiment of the invention, the buzzer 56 is replaced by another sound generator, such as a digital sound-producing circuit. This may comprise a tone generator and a memory. (Tone generators are described in Spraggins, U.S. Pat. No. 4,820,229 (1989).) The tone generator may comprise a central processing unit (CPU) that reads values stored in memory and converts the values contained in memory into analog wave-forms sent to a speaker to reproduce the recorded sound. The memory would preferably be non-volatile so that loss of power does not result in loss of its contents. The memory would preferably be programmable with different sounds.

The sound generating means can comprise an electronic digital sound playback device. Such a device, as is known in the art, has a digitally encoded sound, sound effect, voice, or music stored in memory which is regenerated by a microprocessor and a digital-to-analog converter for playback on a speaker. Such a device can be contained on a single integrated circuit or chip. (Sound chip ISD 1020, can accommodate up to 20 seconds of recorded sound (see Martin, U.S. Pat. No. 5,648,753 (1997)). EPROM digital sampler microchips can also be used.) The sound generating means can also comprise electromechanical sound or noise generators, as well as small analog or digital recording playback devices such as magnetic tape or disk.

Sounds can be programmed using various means, such as the one in Li et al., U.S. Pat. No. 5,768,223 (1998). They described an audio device using control cards to generate signals from a memory module storing digitized audio data Sounds can also be varied using interchangeable cartridges as discussed in Example 13, below.

Sound generators are known and are available in the commercial marketplace. AGC Sound, a subsidiary of Apple Gift Corp., Floral Park N.Y., produces musical, sound effect, and talking modules such as used in greeting cards and other novelty articles, and will make custom circuits.

Sound generators may, of course, be larger. These include magnetic tape players, compact disk players, and radios.

Figure 8:
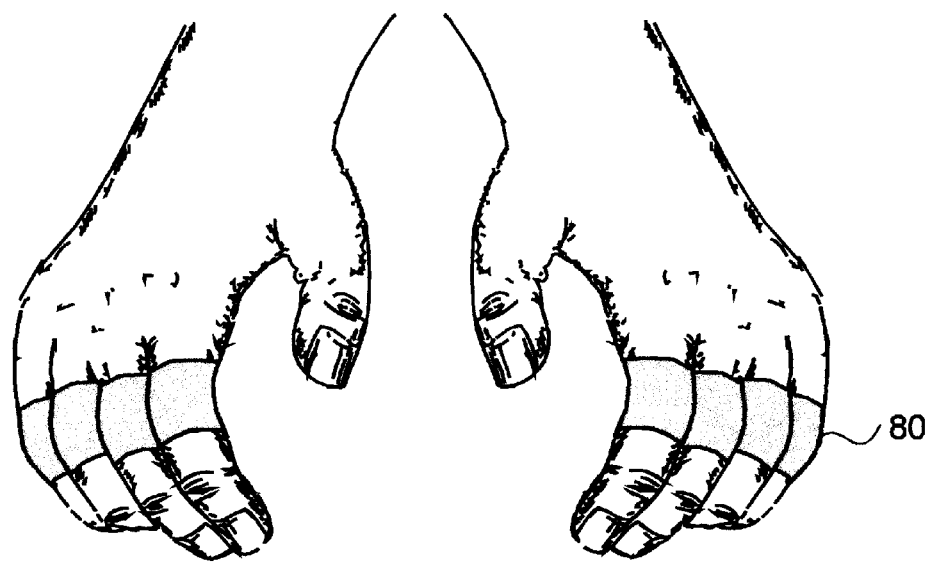
FIG. 8 shows eight cuffs, one worn on each finger.

The sounds may be chosen to be part of a series, such as the eight notes in a scale. FIG. 8 shows eight cuffs, one worn on each finger, each activating a different note, forming a virtual piano. The sounds may be chosen to represent an action and a consequence. For example, two cuffs may be worm, with the first making the sound of screeching tires and the second breaking glass.

The sounds may be chosen to represent phonemes, spoken sounds, or simple words. A set of devices worn on various parts of the body could thus be used to facilitate communication.

EXAMPLE 10

Lights (FIG. 7)

The effect emitters may be light bulbs, light emitting diodes, lasers, or display devices. The lights can form a pattern on the wearable component, such as a sun or animal or a name. A display device can show patterns or pictures or text. FIG. 7 shows the inventive device worn as a cuff on the elbow with such a display 94. The patterns that are lit and the images or text that are displayed depend on the extent or speed of the user's movements, the number of movements made, or on other static or dynamic characteristics of the movement.

EXAMPLE 11

Signal Emitters (FIG. 8)

The effect emitted is an infrared signal or other electromagnetic radiation. The signal is used to control an apparatus, such as light switches or a television on/off switch. The device serves as a wearable remote control. This has the advantages of ease of use and not getting misplaced or in the way. The signals from multiple devices, such as the finger cuffs of FIG. 8, could be used in place of a control pad for Nintendo or Sony type play stations.

EXAMPLE 12

Figure 9:
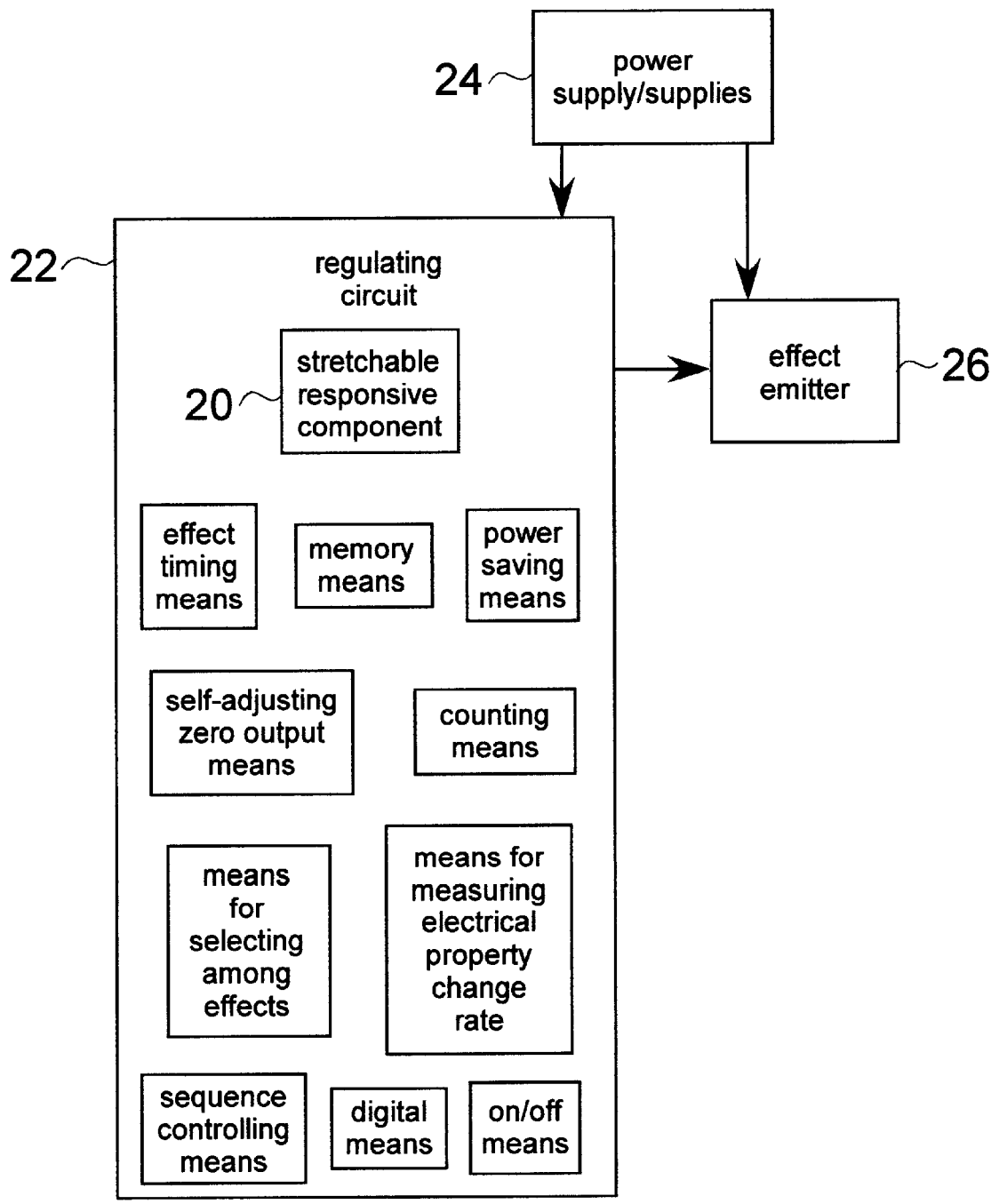
FIG. 9 shows a schematic diagram of the inventive wearable effect emitting device with a more sophisticated regulating circuit.

Circuit Improvements (FIG. 9)

The regulatory circuit can be either analog or digital. An analog example was presented in FIG. 3. An alternative analog circuit would make use of a Wheatstone bridge. Due to their sensitivity, Wheatstone bridge circuits are advantageous for measuring resistance, inductance, and capacitance. Wheatstone bridges are widely used for strain measurements. A quarter bridge consists of four resistors arranged in a diamond orientation. A D.C. voltage is applied between the top and bottom of the diamond and an output voltage is measured across the middle. One of the legs of the bridge may be a strain gauge, and the other legs of the bridge have a resistance equal to that of the strain gauge. When the resistance of the strain gauge changes, a voltage appears across the middle of the bridge.

The use of digital components, such as microprocessors, analog to digital converters, display controllers, and logic chips, greatly expands the possibilities for converting movements into effects.

In other embodiments of the invention, the regulatory circuit is more sophisticated and/or improved, as illustrated in FIG. 9. For example, to reduce power consumption, included within the circuit is a power saver circuit that cuts power to various components when the device is not in use. For another example, an on-off switch is included, or a motion detector is included that automatically turns the device on. The zero adjust may be changed from a mechanical potentiostat to a digital form. The potentiostat, or its equivalent, may be adjusted by the producer, or the device may be constructed so that it can be user adjusted, such as by turning a knob; alternatively, it can be self-adjusting on device start-up.

In another example, the circuit includes a means to allow the user to choose among various sounds in a sound memory module or electromagnetic signals in a memory module, or to choose between different color LEDs. Alternatively, the circuit includes a means to vary the emitted effects depending on the position, velocity, acceleration, history, or other property of the stretching of the responsive component.

In another example, the circuit includes a means to cause various patterns to be displayed on a set of lights or on a display. For instance, the output of the regulating circuit could be connected to multiple lights so that more lights are lighted as the stretching of the responsive component increases.

In another example, the circuit includes a means to operate various effect emitters in sequence or with a particular timing upon stretching the stretchable component. For example, LEDs may be lighted in a particular sequence or may flash at a rate proportional to the degree of stretching.

In another example, the circuit includes a means to measure the speed of the user's movement. This means may be, for example, a differentiator. (Acceleration would use two differentiators.) The output signal to the effect emitter(s) can be made proportional to this speed. Circuits such as these can readily be designed by those skilled in the art. FIG. 7 shows the inventive device worn on the elbow with a display 94 whose output is proportional to the speed of movement of the user, indicated by the lines 90.

In another example, the circuit includes a means to count the number of movements made by the user and to control the emitted effects based on this number. For example, one movement may cause the number 1 to be displayed on an liquid crystal display device, two movements the number 2, etc. Circuits such as these can readily be designed by those skilled in the art with the use of a counting element.

It is to be understood that the above described circuitry is intended to demonstrate, in general, the theory of operation and the electronic circuits used to create the effects of the present invention. There are other ways to combine electronic circuits to accomplish the desired result, and they are intended to be included with the spirit of the present invention, which is not limited to the specific circuitry shown or described.

EXAMPLE 13

Figure 10:
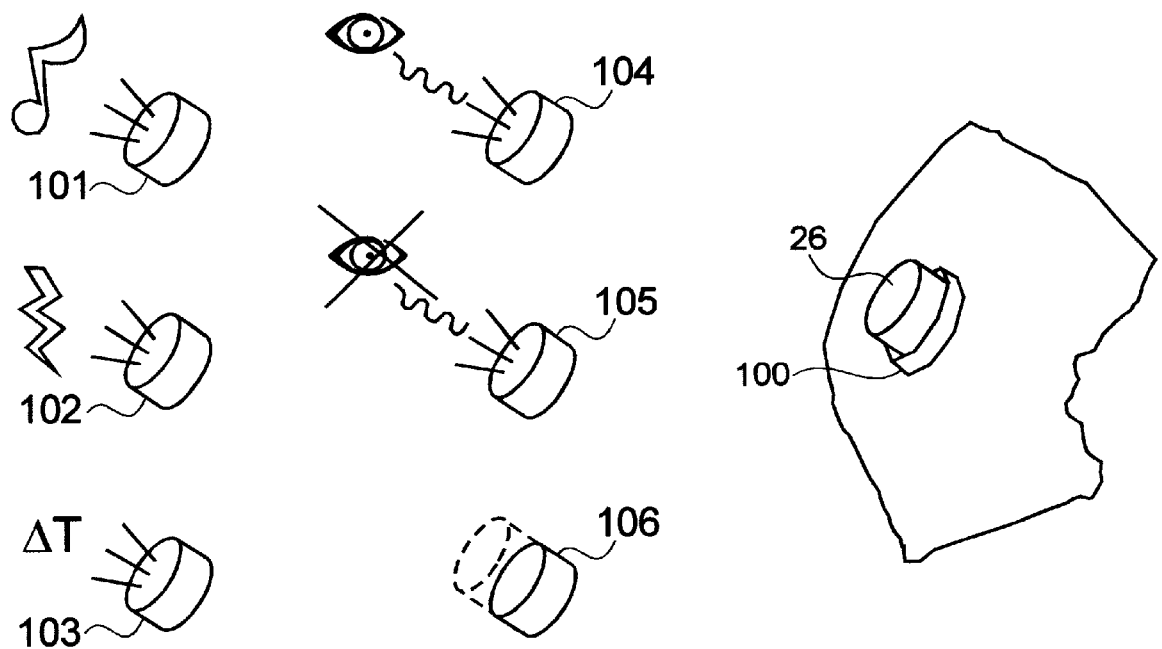
FIG. 10 shows a socket, an exchangeable effect emitter, and various types of effect emitters that can be used in the inventive device.

Exchangeable Effect Emitters (FIG. 10)

As shown in FIG. 10, the wearable component includes one or more sockets 100 into which various effect emitters 26 can be plugged. This allows the user to change, for instance, between different sounds, or between sounds and other effects. Various effect emitting cartridges are also illustrated: sound emitting effect emitter 101, electric shock emitting effect emitter 102, temperature changing effect emitter (heater or cooler) 103, light emitting effect emitter 104, infra-red or radio wave (invisible electromagnetic radiation) emitting effect emitter 105, and movement causing effect emitter (actuator) 106.

EXAMPLE 14

Programmable Effect Emitters

The effect emitter or the regulating circuit includes a means for the manufacturer or user to program the inventive device to various predetermined sounds, images, signals, patterns, etc. Alternatively, the effect emitter or the regulating circuit includes a means for the user to program the inventive device to emit user-defined sounds, images, signals, patterns, etc.

EXAMPLE 15

Incorporation Into Articles (FIG. 11)

Figure 11A:
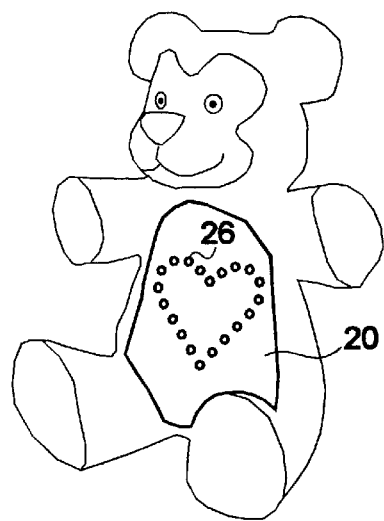
FIG. 11A shows the inventive device incorporated in a stuffed toy.

The inventive device is incorporated into objects. Examples are illustrated in FIG. 11. In FIG. 11A, the stretchable responsive component 20 is the fabric panel that forms the belly of a stuffed toy. (Alternatively, the stretchable responsive component can be placed underneath the fabric that forms the belly.) A heart-shaped pattern of lights is the effect emitter 26. The power supply, circuitry, and interconnecting wiring (not shown) are placed within the stuffed toy so they are not visible from the exterior. Squeezing the stuffed toy or poking its belly cause the heart to light.

Figure 11B:
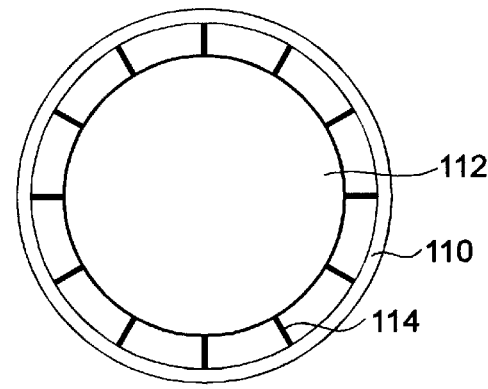
FIG. 11B shows the responsive stretchable component attached within a frame or hoop.

FIG. 11B shows a round central portion 112 attached with attaching means 114 to a frame 110, in this example a hoop-shaped frame. The effect emitters, circuitry, and power supply (not shown) are housed in or on the frame. In one possible embodiment, the central portion 112 is the stretchable responsive component. Deforming it, such as by punching or pinching, causes the effect emitters to activate.

In another possible embodiment, the central portion 112 is a piece of fabric, plastic, or other material, and the attaching means 114 are stretchable responsive components. Displacing the central portion causes the attaching means 114 to stretch, and the effect emitters to activate.

Figure 11C:
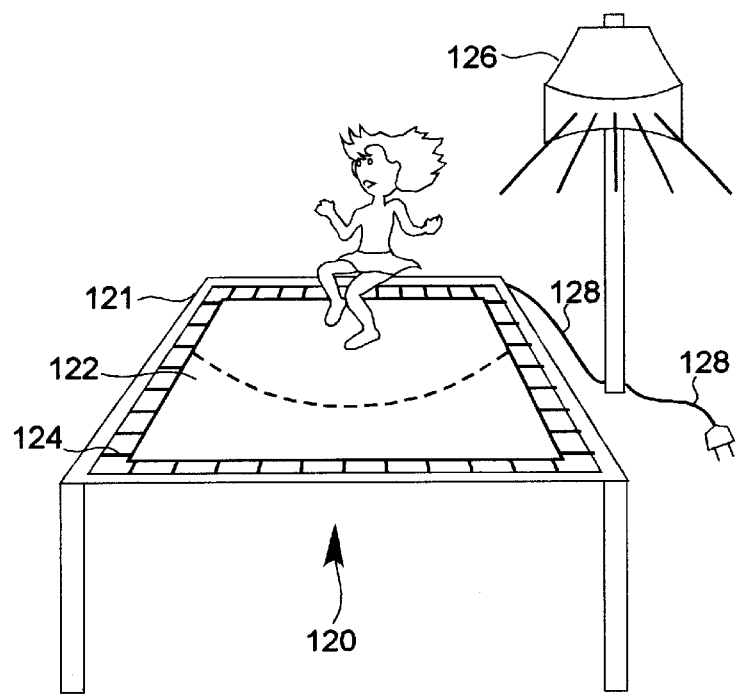
FIG. 11C shows a trampoline into which the inventive device is incorporated.
Figure 11D:
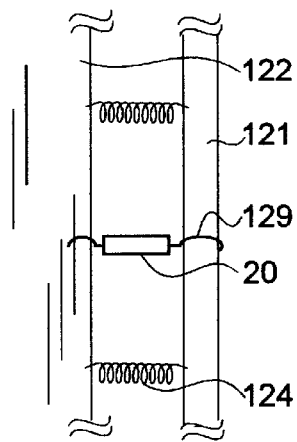
FIG. 11D shows a close-up view of the stretchable component mounted between the trampoline fabric and frame.

FIG. 11C shows a trampoline 120. (This is similar to the device in FIG. 11B.) The stretchable responsive component can be quilted during manufacture to the underside of the trampoline fabric (central portion) 122 or later retrofitted to it. Alternatively, the stretchable responsive component can be attached to the springs or attaching means 124 or strung between the frame 121 and the central portion 122. (The latter is illustrated in FIG. 11D.) With any of the above configurations, jumping on the trampoline causes the responsive component to stretch, causing the regulating circuit (not shown) to send a signal to a sound creating device (not shown) and the loudspeaker 126. The signal from the regulating circuit can be sent to the loudspeaker via a cable or an infrared signal. The device, including the loudspeaker 126, is powered by wall current (110 V or 220 V ac) as shown by the power cord 128. The regulating circuit can alternatively be powered by batteries or other means.

FIG. 11D shows a close-up view of the trampoline fabric 122, the frame 121, and the attaching means 124 (in this example shown as springs). The responsive stretchable component 20 is attached between the fabric 122 and the flame 121 using two hooks 129. (The circuit and connecting leads are not shown.) With this configuration, which is similar to that shown in FIG. 6B, any trampoline can be retrofitted with the inventive effect-emitting device. Similarly, many other moving objects or moving parts could be so retrofitted, using attaching means such as hooks, adhesive tape, snaps, buttons, hook-and-loop fasteners, etc.

EXAMPLE 16

Figure 12:
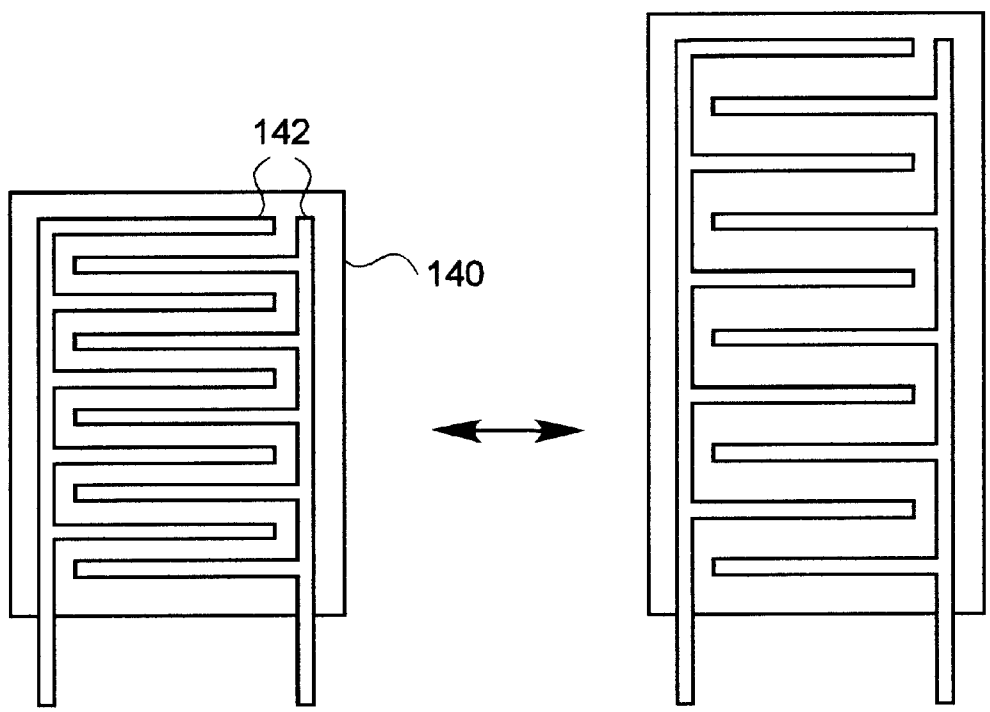
FIG. 12 shows a stretchable component that changes capacitance.

Other Electrical Properties (FIG. 12)

In another embodiment, the responsive component changes capacitance or inductance when stretched. Alternatively, the complex impedance is changed when it is stretched. Thus, the circuit may detect a change in the RC time constant, or a change in the phase of an a.c. waveform.

FIG. 12 shows one example of a stretchable capacitance-changing component. A stretchable dielectric 140 has interdigitated ion implanted regions142; the implanted regions are rendered conducting and thus serve as electrodes. Alternatively, the dielectric is impregnated with a conducting conjugated polymer in interdigitated electrode regions. The dielectric 140 may be a rubber, either natural or synthetic (such as acrylonitrile-butadiene-styrene). When the rubber is stretched in the direction perpendicular to the electrode fingers, the separation d between the fingers changes. Capacitance is given by $\in A/d$, where $\in$ is the dielectric constant, A the cross-sectional area of the finger, and d the finger separation. Thus, a change in d results in a change in capacitance. Such capacitance measurements and electrode geometries are frequently used in the silicon industry to measure tiny changes in electrode separation (and therefore strain). Stasiuk, in Calif. 2184957 (laid open 1998), described a capacitive compressive sensor in which a load caused the separation of conducting plates to decrease. Here, the separation of the conductors increases upon stretching. The capacitance of a conjugated polymer coated fabric would also be expected to change upon stretching because the separation between conducting fibers decreases. Likewise, the change in the weave upon stretching would be expected to change the inductance of the fabric. Instead of, or in addition to, detecting the change in resistance, the change in capacitance or inductance can be detected.

When the current in a conductor varies, the resulting changing magnetic field cuts across the conductor itself and induces a voltage in it. This self-induced voltage is opposite to the applied voltage and tends to limit or reverse the original current. An inductance coil tends to smooth out a varying current. The inductance is determined by the geometry of the coil and the magnetic properties of its core. The inductance for a circular coil of wire is given by $L=N^2 R \mu_0 \mu_r [\ln(8R/a)-2]$, where N is the number of turns, R is the radius of the loop, $\mu_0 \mu_r$ is the permeability of the surrounding medium, and a is the radius of the wire. Changing the radius R, such as by stretching the coil, would change the inductance L. Thus, a stretchable medium, such as a rubber, with an imbedded conducting coil can be used in the present invention Although the invention has been described above with reference to particular examples, it is to be understood that other embodiments are possible and contemplated within the scope of the present invention as defined in the appended claims.

Conclusions, Ramifications, and Scope of the Invention

The inventive wearable effect-emitting device is a simple, but quite useful, employment of conducting polymers or conducting polymer coated materials. This device does not depend on a computer for position reading; rather, it is done locally, one stretch location at a time. A wearer is free to use the device in any location because it is portable, light weight, unobtrusive, and comfortable. Thus, effects are produced without hindering the normal movements of the wearer during play, training, or other use. The effects arise from the wearer's movements, even if those movements are very small, without the need to press buttons. This not only allows children to play naturally with the device, but is also a boon to those with limited or weak movement capability, for example due to atrophy. The effects can be made dependent on the magnitude or speed of the wearer's movements, or the number of movements, allowing a range of interesting effects and applications. The effect emitting device can be worn on any number of body parts, allowing the entire body to participate. This has really good play value, as well as being of interest to the sports person. The ability to miniaturize the device adds to the number of body parts that can be used. Because the device is simple, requiring only a few components, it is inexpensive to manufacture. Although the inventive device is wearable, it is not necessarily worn on a person or other living thing, but can be incorporated into articles (such as shown in FIG. 11), which extends the applications even further.

The inventive device can be used in a number of application areas. We discuss some of these applications now.

Applications: Toys

As a toy, this simple device is used to provide amusement, either as a single unit or in combination with other units. For example, in FIG. 4A the device is worn as a band around the knee and in FIG. 8 around the fingers. Such a finger-band can be used to make a gun shooting sound. A band worn on the knees can be used to make sounds of cars or motorcycles when a person is running. Two arm bands can be used together, one to make a first sound, such as brakes screeching, and the other to make a second sound related to the first, such as a crash. A number of bands worn all over the body can produce a sound and light display coordinated with dancing. Bands worn on multiple fingers create a "virtual piano" or other musical instrument. In addition to bands or cuffs, other wearable forms may also be used, including gloves, shirts, ski masks, pants, socks, strips with adhesive ends, etc. A plurality of the inventive devices can be incorporated into a body-suit at numerous bendable or extensible body positions, so that the suit can generate various effects from the entire body.

The sound volume can be linked to the extent of the resistance drop, which is controlled by the amount of bending. Thus, sound volume can be directly modulated by limb bending degree. Similarly, light brightness can be controlled. Sound/light/other effects can be generated while running, wiggling fingers, dancing, or other activities.

A wide variety of sounds that are fun for different children can be programmed into a sound module. The devices could come with a standard socket for holding lights and/or sounds. Various groups of effect emitters can be sold as sets.

Alternatively, a single sound module may be programmed to emit different sounds. This could be achieved by using an optical scanner and a set of bar codes, or by an insertable card. Another method would be to first download a sound from a computer, tape recorder, etc. to a memory associated with the sound module. Li et al., U.S. Pat. No. 5,768,223 (1998), describe an audio device for a toy using control cards to control signals from a memory module storing digitized audio data. In addition, Eskildsen, U.S. Pat. No. 5,962,839 (1999) describes a device with a reading member for reading bar codes, each code representing an action; a computer can generate the codes.

A more complex effect emitter may be envisioned. For example, for older children a small liquid crystal display (LCD) could be programmed to show different images.

Application: Biofeedback

Because the device is sensitive to body movement, it is readily applied to biofeedback purposes. In one such embodiment, it can be used for the correction of posture. When the back is not straight, the responsive component will be stretched relative to when the back is straight, which will generate a signal to the wearer (FIG. 6). This can be useful to athletes who want to train themselves to take a certain stance, such as a golfer (FIG. 13); if the limbs are not in the right position, as set by the user, then the user will hear a sound. It can also be useful in providing feedback on motions, such as a golf swing or belly dancing, by providing an auditory signal characteristic of the motion.

For another example, biofeedback uses of the device are helpful during rehabilitation. It can be used to monitor the function of a limb, indicating by loudness whether more motion is being achieved. Because of the sensitivity of the responsive component and the amplification provided by the circuit, even small motions are detectable. Together with a user-controlled set point, the device could therefore be used to monitor small improvements.

Application: Communication

Severely disabled people sometimes have a limited use of only a few muscle groups. The device in this patent could be used on various parts of the body, such as in the form of patches. In this case, the auditory signals might be used directly to synthesize crude speech, or an infrared light coupled with a detector could be used to communicate via a computer.

Application: Control

A signal produced by the wearable effect emitting device is used to control other devices and apparatuses (stereo, TV, or room lights), either by auditory, light, or infrared signals. These are easier to use and harder to lose.

Application: Monitoring

Devices placed on infants or disabled or comatose persons are used to signal their movements. This is useful for monitoring, diagnosis, or treatment.

Application: Training

Biofeedback can be used for trainnig of muscles. For example, to teach oneself to wiggle one's ears usually requires practice in front of a mirror. This auditory signal provided by a headband or by ear muffs or a hat could be used instead.

Figure 13:
FIG. 13 shows a body suit worn by a golfer with the inventive device incorporated at the shoulders, elbows, and wrists.

The inventive device could be used to improve sports and dance motions. The devices may be incorporated in a body suit at several positions, such as shoulders, elbows, and wrists (FIG. 13). The particular sequence, duration, and loudness of sounds during the movement, for example a golf swing, would be helpful in improving the movement. The sounds of an ideal movement may be recorded by professionals for comparison. The user would try to emulate the ideal sound as part of the training.

I claim:

1. An effect-emitting strain gauge device comprising:
   an electrically conductive fabric capable of changing its electrical properties in response to stretching or relaxing;
   a signal control circuit coupled with the electrically conductive fabric, the signal control circuit outputting a signal corresponding to the electrical properties of the electrically conductive fabric; and
   at least one effect-emitting device coupled with the signal control circuit, the at least one effect-emitting device receiving the signal from the signal control circuit and emitting an effect according to the signal.

2. An effect-emitting strain gauge device according to claim 1, further comprising means for attaching the device to a body.

3. An effect-emitting strain gauge device according to claim 2, wherein the electrical properties of the electrically conductive fabric change according to movement or a position of the body.

4. An effect-emitting strain gauge device according to claim 3, wherein the signal output by the signal control circuit varies with the position of the body.

5. An effect-emitting strain gauge device according to claim 3, wherein the signal output by the signal control circuit varies depending on at least one of speed, acceleration and number of movements by the body.

6. An effect-emitting strain gauge device according to claim 1, wherein the electrically conductive fabric comprises coated fibers.

7. An effect-emitting strain gauge device according to claim 1, wherein the electrical properties comprise resistance.

8. An effect-emitting strain gauge device according to claim 1, wherein the electrical properties comprise one of capacitance, inductance and impedance.

9. An effect-emitting strain gauge device according to claim 1, wherein the effect emitted by the at least one effect-emitting device comprises at least one of sound, light, infrared light, radio frequency electromagnetic radiation, electric shock, movement, and change in temperature.

10. An effect-emitting strain gauge device according to claim 9, where a sound emitting effect-emitting device comprises one of a music synthesizer, a sound chip, an interchangeable sound cartridge, a magnetic tape player, a compact disk player, and a radio.

11. An effect-emitting strain gauge device according to claim 9, where a light emitting effect-emitting device comprises one of light bulbs, light emitting diodes, lasers, and displays.

12. An effect-emitting strain gauge device according to claim 1, further comprising a power source coupled with the signal control circuit, the power source comprising one of batteries, solar cells, a.c. wall current, self-winding watch type generators, and springs.

13. An effect-emitting strain gauge device according to claim 1, wherein the effect emitted by the at least one effect-emitting device is varied in proportion to a change in the electrical properties of the electrically conductive fabric.

14. An effect-emitting strain gauge device according to claim 1, wherein the signal control circuit compares the electrical properties of the electrically conductive fabric to a set value so that an effect is generated by the at least one effect-emitting device if the electrical properties deviate from the set value.

15. An effect-emitting strain gauge device according to claim 1, further comprising means for selecting among emitted effects.

16. An effect-emitting strain gauge device according to claim 15, further comprising means for controlling a sequence of the emitted effects.

17. An effect-emitting strain gauge device according to claim 15, wherein the at least one effect-emitting device comprises means for controlling timing of the emitted effects.

18. An effect-emitting strain gauge device according to claim 1, further comprising means for detecting a rate of change of the electrically conductive fabric's electrical properties.

19. An effect-emitting strain gauge device according to claim 1, comprising a plurality of effect-emitting devices, the effect-emitting strain gauge device further comprising a socket selectively receiving at least one of the effect-emitting devices.

20. An effect-emitting strain gauge device according to claim 1, wherein the at least one effect-emitting device is used in combination with at least one of playthings, games, books, sports equipment, decorations, educational tools, recreational equipment, and medical apparatus.

21. An effect-emitting strain gauge device according to claim 1, wherein the electrically conductive fabric is made from one of conjugated polymer-coated fibers, metal-coated fibers, carbon-coated fibers, polypyrrole-coated fibers, and polyaniline-coated fibers.

* * * * *

UNITED STATES PATENT AND TRADEMARK OFFICE
CERTIFICATE OF CORRECTION

PATENT NO. : 6,360,615 B1
DATED : March 26, 2002
INVENTOR(S) : Smela

It is certified that error appears in the above-identified patent and that said Letters Patent is hereby corrected as shown below:

<u>Title page,</u>
Item [56], please add the following References Cited:
    U.S. PATENT DOCUMENTS

| | | |
|---|---|---|
| 3,297,021 | 1/1967 | Davis et al. |
| 3,648,372 | 3/1972 | Kirschenbaum |
| 3,929,335 | 12/1975 | Malick |
| 4,121,453 | 10/1978 | Levin et al. |
| 4,306,571 | 12/1981 | McLeod, Jr. |
| 4,426,884 | 1/1984 | Polchaninoff |
| 4,444,205 | 4/1984 | Jackson |
| 4,501,148 | 2/1985 | Nicholas et al. |
| 4,586,495 | 5/1986 | Petrofsky |
| 4,777,477 | 10/1988 | Watson |
| 4,865,610 | 9/1989 | Muller |
| 4,905,560 | 3/1990 | Suzuki et al. |
| 5,052,375 | 10/1991 | Stark et al. |
| 5,143,505 | 9/1992 | Burdea et al. |
| 5,184,319 | 2/1993 | Kramer |
| 5,280,265 | 1/1994 | Kramer et al. |
| 5,295,490 | 3/1994 | Dodakian |
| 5,301,678 | 4/1994 | Watson et al. |
| 5,368,546 | 11/1994 | Stark et al. |
| 5,454,376 | 10/1995 | Stephens et al. |
| 5,484,389 | 1/1996 | Stark et al. |
| 5,651,671 | 7/1997 | Seay et al. |
| 5,775,332 | 7/1998 | Goldman |
| 5,823,975 | 10/1998 | Stark et al. |
| 5,858,291 | 1/1999 | Li et al. |
| 5,929,782 | 7/1999 | Stark et al. |
| 5,989,157 | 11/1999 | Walton |
| 6,042,555 | 3/2000 | Kramer et al. |
| 6,155,120 | 12/2000 | Taylor |
| 6,184,797 | 2/2001 | Stark et al. |
| 6,216,545 | 4/2001 | Taylor |

OTHER PUBLICATIONS
Post, E. R. et al., "E-broidery: Design and Fabrication of Textile-Based Computing", IBM Systems Journal, Vol. 39, Nos. 3 & 4, 2000, pp. 840-860.

Rensselaer Alumni Magazine, "My Body, My Instrument: Mixing Motion and Sound", September, 2001, p. 4.

UNITED STATES PATENT AND TRADEMARK OFFICE
CERTIFICATE OF CORRECTION

PATENT NO. : 6,360,615 B1
DATED : March 26, 2002
INVENTOR(S) : Smela

It is certified that error appears in the above-identified patent and that said Letters Patent is hereby corrected as shown below:

Column 20,
Line 38, please add claim 22 as follows:
22. A method for producing an effect comprising the steps of:
(a) stretching or relaxing an electrically conductive fabric;
(b) detecting an electrical property of said electrically conductive fabric, the electrical property varying according to the stretching and relaxing of the electrically conductive fabric;
(c) generating an electrical signal based on said electrical property; and
(d) controlling an effect emitting device according to said signal.

Signed and Sealed this

Twelfth Day of November, 2002

Attest:

*Attesting Officer*

JAMES E. ROGAN
*Director of the United States Patent and Trademark Office*